(12) United States Patent
O'Young et al.

(10) Patent No.: US 10,336,672 B2
(45) Date of Patent: Jul. 2, 2019

(54) SYSTEM AND METHOD FOR PRODUCING NEOPENTYL GLYCOL

(71) Applicants: ClearWaterBay Technology, Inc., Pomona, CA (US); ClearWaterBay Technology, Ltd., New Territories OT (HK)

(72) Inventors: Drow Lionel O'Young, Walnut, CA (US); Christianto Wibowo, Chino Hills, CA (US); Yik Chung Chan, Hong Kong (CN)

(73) Assignees: ClearWaterBay Technology, Inc., Walnut, CA (US); ClearWaterBay Technology, Ltd., New Territories (HK)

( * ) Notice: Subject to any disclaimer, the term of this patent is extended or adjusted under 35 U.S.C. 154(b) by 345 days.

(21) Appl. No.: 14/817,059

(22) Filed: Aug. 3, 2015

(65) Prior Publication Data
US 2016/0031775 A1    Feb. 4, 2016

Related U.S. Application Data

(60) Provisional application No. 62/032,950, filed on Aug. 4, 2014.

(51) Int. Cl.
*C07C 45/75*     (2006.01)
*C07C 29/141*    (2006.01)

(52) U.S. Cl.
CPC ............ *C07C 29/141* (2013.01); *C07C 45/75* (2013.01); *B01J 2219/00006* (2013.01)

(58) Field of Classification Search
CPC .................................................. C07C 29/141
See application file for complete search history.

(56) References Cited

U.S. PATENT DOCUMENTS

| | | |
|---|---|---|
| 2,818,443 A | 12/1957 | Robeson |
| 2,895,996 A | 7/1959 | Wright, Jr. et al. |
| 3,808,280 A | 4/1974 | Merger et al. |
| 3,920,760 A | 11/1975 | Heinz |
| 3,939,216 A | 2/1976 | Wright |
| 4,021,496 A | 5/1977 | Wright |
| 4,036,888 A | 7/1977 | Couderc et al. |
| 4,855,515 A | 8/1989 | Morris et al. |
| 4,933,473 A | 6/1990 | Ninomiya et al. |
| 4,935,555 A | 6/1990 | Elias et al. |
| 5,144,088 A | 9/1992 | Salek et al. |
| 5,146,012 A | 9/1992 | Salek et al. |
| 5,185,478 A | 2/1993 | Salek et al. |
| 5,395,989 A | 3/1995 | Yoneoka et al. |
| 5,532,417 A | 7/1996 | Salek et al. |
| 5,841,002 A | 11/1998 | Harrison et al. |
| 6,201,159 B1 | 3/2001 | Choi et al. |
| 6,268,539 B1 | 7/2001 | Sen-Huang et al. |
| 7,767,665 B2 | 8/2010 | Sirch et al. |
| 8,394,998 B2 | 3/2013 | Schalapski et al. |
| 2006/0264679 A1 | 11/2006 | Haubner et al. |
| 2010/0113836 A1 | 5/2010 | Sirch et al. |
| 2011/0098515 A1 | 4/2011 | Schalapski et al. |
| 2012/0271029 A1 | 10/2012 | Kronemayer et al. |

FOREIGN PATENT DOCUMENTS

CN     103130611 A    6/2013

OTHER PUBLICATIONS

International Search Report and Written Opinion in International Application No. PCT/US2015/043672, dated Nov. 4, 2015.
Barnicki, S.D., "Synthetic Organic Chemicals", Chapter 10, In Handbook of Industrial Chemistry and Biotechnology, pp. 307-389, 2012.

*Primary Examiner* — Ana Z Muresan
(74) *Attorney, Agent, or Firm* — Nixon Peabody LLP

(57) ABSTRACT

The present invention describes a process for production of neopentyl glycol (NPG) from formaldehyde (FD) and isobutyraldehyde (IBD). FD and IBD first react to form hydroxypivaldehyde (HPD) in an aldol condensation step, then HPD is hydrogenated to form NPG in a hydrogenation step. The aldol condensation step is performed using a solid catalyst such as an ion exchange resin catalyst, which can be easily separated from the reaction product. The feed to the aldol condensation step is made homogeneous by adjusting the ratio of IBD, FD, and water in the feed or by adding a solvent that is miscible with both IBD and water. High purity NPG is recovered from the product of the hydrogenation step by a suitable method such as crystallization.

11 Claims, 2 Drawing Sheets

SYSTEM AND METHOD FOR PRODUCING NEOPENTYL GLYCOL

CROSS REFERENCE TO RELATED APPLICATION

This application claims the benefit of, and priority to U.S. Provisional Patent Application Ser. No. 62/032,950, filed Aug. 4, 2014, titled System and Method for Producing Neopentyl Glycol, the entire disclosure of which is hereby incorporated by reference.

FIELD OF THE INVENTION

The present invention relates to the production of neopentyl glycol (NPG) from formaldehyde and isobutyraldehyde. More specifically, the present invention relates to a method and system for production of NPG, in which a solid catalyst such as an ion exchange resin catalyst is used to perform aldol condensation reaction, and in which a solvent is added to the feed of the aldol condensation reactor to produce a homogeneous liquid phase.

BACKGROUND

Neopentyl glycol (NPG, IUPAC name 2,2-dimethyl-1,3-propanediol) is an important industrial intermediate used in the synthesis of polyesters, especially resins for airplane or boat manufacturing. The neopentyl structure provides excellent resistance to light, heat, and hydrolysis. NPG is also being used in a variety of formulations in varnish coatings, synthetic lubricants, and plasticizers.

Methods for producing NPG is well-known in the prior art. For example, U.S. Pat. No. 4,855,515 (Eastman Kodak Company) described a two-step method for producing NPG. The first step is aldol condensation reaction of formaldehyde (FD) and isobutylaldehyde (IBD) to form an intermediate product hydroxypivaldehyde (HPD), which is then hydrogenated to NPG in the second step.

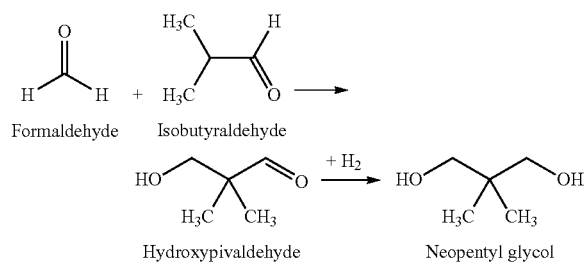

It is also known from the prior art that the aldol condensation reaction is typically performed in the presence of a basic catalyst, while the hydrogenation reaction can be conducted with a typical hydrogenation catalyst such as Raney Nickel, as disclosed in U.S. Pat. No. 2,818,443 (Celanese Corporation of America), U.S. Pat. No. 3,920,760 (Eastman Kodak Company), U.S. Pat. No. 5,841,002 (Davy Process Technology Limited), U.S. Pat. No. 6,201,159 (LG Chemical Limited), U.S. Pat. No. 6,268,539 (Nan Ya Plastics Corporation), and U.S. Pat. No. 8,394,998 (Oxea GmbH). The use of other catalysts have also been disclosed; for example, U.S. Pat. No. 5,395,989 (Mitsubishi) teaches the use of CuO—ZnO—ZrO mixture as catalyst, while U.S. Pat. No. 5,532,417 (Aristech Chemical) suggests copper chromite.

If a strong alkali such as sodium hydroxide or calcium hydroxide is used, the hydrogenation step can be eliminated by using excess formaldehyde to convert HPD to NPG via cross-Cannizzaro reaction (Barnicki, 2012), resulting in essentially a one-step method to produce NPG from FD and IBD, in which the strong alkali is both a catalyst and a reactant.

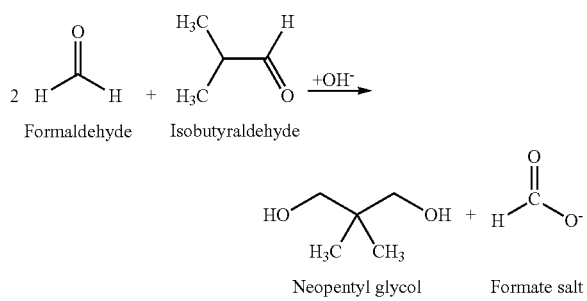

Although this method only requires one reactor, it produces a formate salt such as sodium formate as a by-product, which is undesirable for commercial scale manufacturing. Furthermore, a more involved separation process will be required to recover NPG.

The use of a sodium compound as aldol condensation catalyst in the two-step method also leads to the need of a complex separation process, because the sodium compound has to be completely removed prior to hydrogenation to avoid poisoning of the hydrogenation catalyst. For example, U.S. Pat. No. 3,920,760 (Eastman Kodak Company) describes a separation process involving filtration, decantation, and coalescence in order to remove sodium compounds after aldol condensation. Therefore, it is more desirable to use a catalyst that does not contain sodium. For example, U.S. Pat. No. 3,808,280 (BASF) teaches about the use of a tertiary alkylamine as the aldol condensation catalyst. Since an aqueous formalin solution is normally used as the source of FD, while IBD is not miscible with water, the reaction system consists of two liquid phases, and the tertiary alkylamine also acts as a phase transfer catalyst which facilitates the reaction. U.S. Pat. No. 2,818,443 (Celanese Corporation of America) proposes the use of a weak basic ion exchange resin (IER), which can be easily separated from the intermediate product, thereby minimizing separation effort. However, an extra solvent such as methanol or other aliphatic alcohols has to be added to homogenize the solution. Another alternative to avoid liquid-liquid phase separation is to use paraformaldehyde instead of formalin as the source of fomaldehyde so that water is not present in the system, as disclosed in U.S. Pat. Nos. 5,144,088, 5,146,012, 5,185,478, and 5,532,417 (Aristech Chemical Cooperation).

In order to obtain NPG in a highly pure form, it is required to remove by-products that are generated from either the aldol condensation or hydrogenation reaction. U.S. Pat. No. 6,201,159 (LG Chemical Limited) discloses a process for the production of NPG that involves extraction and distillation steps to isolate HPD prior to hydrogenation, and a saponification step followed by another set of extraction and distillation steps to obtain highly pure NPG after hydrogenation. Saponification with caustic is useful to remove ester impurities from NPG, but the caustic-containing mixture is unstable at high temperatures, so that steam sublimation or film evaporation is usually required, as suggested in U.S. Pat. No. 4,935,555. The complexity of the separation process potentially leads to high capital cost and energy consumption. A simpler separation process prior to hydrogenation has also been suggested. For example, U.S. Pat. No. 4,036,888 (Societe Chimique des Charbonnages) and U.S. Pat. No. 5,144,088 (Aristech Chemical Cooperation) suggest the use of crystallization for isolating HPD after the aldol condensation reaction. However, this alternative also requires a relatively high energy consumption since the HPD crystals have to be melted before the hydrogenation step.

Accordingly, further developments and improved processes are greatly needed.

SUMMARY OF THE INVENTION

Accordingly, the present invention provides an improved process for the production of NPG. In some embodiments, a method is provided, comprising the steps of: controlling the composition of the feed to a first reaction step, which consists primarily of IBD and FD, but may also contain water and methanol, by adjusting the ratio of IBD, FD, and water or by adding a solvent that is miscible with both isobutyraldehyde and water;

reacting the mixture in an aldol condensation reactor where IBD and FD react to form HPD in the presence of a suitable solid, such as for example without limitation an ion exchange resin catalyst;

separating excess and unreacted aldehydes from the reaction mixture and recycling the aldehydes to the aldol condensation reactor;

contacting HPD with hydrogen in a hydrogenation reactor, where it is converted to NPG in the presence of a suitable hydrogenation catalyst;

isolating highly pure NPG from the reaction mixture from the hydrogenation reactor; and recovering the solvent from the reaction mixture from the hydrogenation reactor, so that the solvent is recycled.

In another embodiment, a system for producing neopentyl glycol from isobutyraldehyde, formaldehyde, and hydrogen is provided, comprising: a feed stream comprising a homogeneous solution; an aldol condensation reactor which receives the homogeneous solution and in a first reaction step at least a portion of the isobutyraldehyde and formaldehyde undergo an aldol condensation reaction to form a reaction mixture comprising hydroxypivaldehyde, in the presence of a suitable solid catalyst; a first separator where excess and unreacted aldehydes from the reaction mixture are separated and the aldehydes are recycled to the aldol condensation reactor; a hydrogenation reactor which receives the reaction mixture and contacts hydroxypivaldehyde with hydrogen in a second reaction step, where hydroxypivaldehyde is converted to neopentyl glycol in the presence of a suitable hydrogenation catalyst; and a second separator where highly pure neopentyl glycol from the reaction mixture from the hydrogenation reactor is separated and solvent from the reaction mixture from the hydrogenation reactor is recovered.

BRIEF DESCRIPTION OF THE DRAWINGS

Other aspects, embodiments and advantages of the invention will become apparent upon reading of the detailed description of the invention and the appended claims provided below, and upon reference to the drawings in which:

DETAILED DESCRIPTION OF THE INVENTION

In the first reaction step, isobutyraldehyde and formaldehyde are reacted to form HPD via an aldol condensation reaction in the presence of a solid catalyst. More particularly, the catalyst may be an ion exchange resin (IER) catalyst such as an Amberlite (trademark) resin, a zeolite, or any other suitable catalyst. The IER catalyst can be accommodated in a suitable type of reactor such as a packed bed reactor or trickle bed reactor, which does not require an additional step for catalyst separation. The main reaction can be written as

$$IBD+FD \rightarrow HPD \quad (1)$$

The temperature, pressure, and the catalyst volume provided in the first reaction step are chosen in order to achieve a suitable per pass conversion of FD, which gives a high selectivity to HPD and minimizes the formation of byproducts. Higher temperatures are known to damage the IER catalyst, hence mild conditions are preferred. However, the temperature may be chosen so as to achieve the desired FD conversion using an economically feasible volume of catalyst. Accordingly, the first reaction step may be operated at a temperature of from 40° C. to 100° C., preferably from 60° C. to 90° C., and a pressure of from 1 bar to 5 bar, preferably from 1 bar to 3 bar. The molar ratio of IBD and FD in the feed to the first reaction step may be anywhere between 0.8:1 and 4:1, preferably between 1:1 and 2:1.

According to one embodiment of the present invention, a homogeneous solution containing IBD and FD needs to be created prior to this reaction step. Since FD is typically available as formalin, which is a solution of FD in water with some methanol added as stabilizer, mixing a stoichiometric amount of IBD and FD leads to a mixture consisting of two liquid phases. In order to conduct the reaction using an ion exchange resin catalyst, it is necessary to make this mixture homogeneous. This can be achieved by either adjusting the ratio of IBD, FD, and water in the feed, or adding a solvent that is miscible with both IBD and water, such that the overall composition falls outside the two-phase region at the desired reaction temperature.

A general description of the liquid-liquid phase equilibrium (LLE) behavior for this system is now described. The existence of a liquid-liquid phase split depends on the thermodynamic properties of the components in the mixture, as well as the temperature and pressure. The LLE behavior of a system can be represented on a phase diagram. For a three component system at a fixed temperature and pressure, the phase diagram takes the shape of a triangle, with the component compositions in weight fraction plotted on a triangular grid. The range of compositions under which a phase split is observed is defined by an enclosed region ('LLE envelope') within the plot.

Figures 1A, 1B:
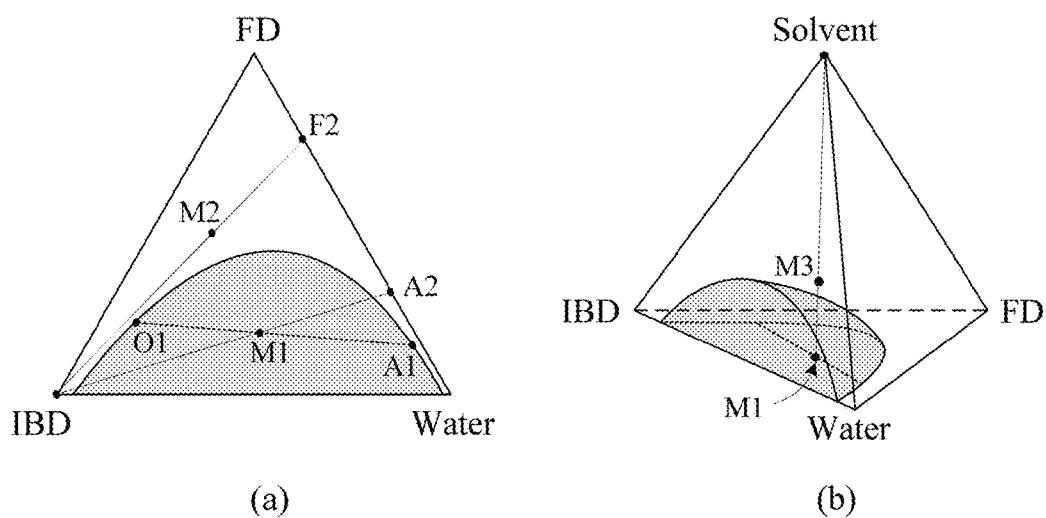
FIG. 1(a) shows a phase equilibrium diagram for a ternary system of IBD, FD, and water.
FIG. 1(b) shows a phase equilibrium diagram for a quaternary system of IBD, FD, water, and a solvent, where the solvent is miscible with both IBD and water.

FIG. 1(a) shows the sketch of a LLE phase diagram for a system comprising IBD, FD, and water at a fixed pressure and temperature. Pure IBD and pure water are completely miscible with FD; however, IBD and water are not fully miscible with each other. Any composition of the mixture of IBD, FD, and water is represented by a point within the triangle shown in the figure. It should be understood by those of ordinary skill in the art that the system may include other components or solutes such as impurities and the like; however, for purposes of the present invention we are concerned only with the primary components in the solution—IBD, FD, and water.

The shaded area represents the LLE envelope in which liquid-liquid phase split will occur. Any composition outside this region is completely miscible and forms a single phase. Any composition within this region forms two liquid phases—a water rich aqueous phase, and an IBD-rich organic phase. The compositions of the two phases are shown by points where the 'tie-line' passing through the mixture composition meets the boundary of the LLE envelope. For example, if IBD is mixed with an aqueous solution of formaldehyde with a composition denoted by point F1 in the figure to produce an overall mixture composition denoted by point M1 in the figure, a phase split into an organic phase O1 and an aqueous phase A1 will occur. On the other hand, mixing IBD with another mixture of formaldehyde and water with a composition denoted by point 2 in the figure will result in a mixture with a composition outside the LLE envelope, such as point M2 in the figure. According to the present invention, controlling the relative amount of IBD, FD, and water in the feed such that the overall mixture falls outside the LLE envelope is one of the ways of producing a homogeneous feed to the aldol condensation reactor. This can be done by using a different raw material, such as paraformaldehyde instead of formalin solution as a source of FD.

A homogeneous solution containing IBD, FD, and water can also be obtained by adding a solvent that is miscible with both IBD and water. Referring specifically to FIG. 1(b), a sketch of the phase diagram of a quaternary system involving IBD, FD, water, and the said solvent is shown. The shaded three-dimensional region represents the LLE envelope at a fixed temperature, in which liquid-liquid phase split will occur. Starting with a mixture of IBD, FD, and water inside the LLE envelope, such as point M1 in the figure, a suitable amount of solvent can be added to bring the composition of the overall mixture outside the LLE envelope, such as point M2 in the figure, so that the overall mixture becomes homogeneous. According to the present invention, the size of the LLE envelope can be controlled by selecting a suitable solvent, such that the required amount of solvent to produce a homogeneous mixture can be minimized. Potentially suitable solvents include, but are not limited to: methanol, ethanol, isopropanol, ethylene glycol, propylene glycol, and NPG.

In a preferred embodiment of this invention, NPG is used as the solvent. Since NPG is the final product, using NPG as the solvent offers an advantage of not having to introduce an additional component to the system. Furthermore, the amount of NPG in the feed to the aldol condensation reactor only needs to be in the range of 10-30 percent by weight to make a homogeneous feed. Therefore, there is no need for a large recycle stream for the solvent, and the size of the reactor can be significantly smaller. Moreover, since NPG has a high boiling point, it will be recycled from the bottom of distillation column (if distillation is used). Compared to using other low boiling components as the solvent, the energy requirement for the system using NPG is much lower. On the other hand, if crystallization is used as the separation method, the NPG-rich mother liquor can serve as the solvent for the aldol condensation reaction.

Apart from reaction (1) there may also be side reactions which produce byproducts such as carboxylic acids and esters, so that the outlet stream from the first reaction step contains unreacted IBD, unreacted FD, HPD, and the byproducts. This stream is sent to a separation system to recover the unreacted aldehydes so that they can be recycled to the reactor. A suitable separation method such as distillation can be used in the separation system.

In the second reaction step, the mixture from the first reaction step is contacted with hydrogen to form NPG in the presence of a catalyst. More particularly, the catalyst may be any suitable hydrogenation catalyst such as copper chromite or ruthenium on activated carbon. The main reaction occurring in the second reaction step is:

$$HPD + H_2 \rightarrow NPG \qquad (2)$$

There may also be side reactions which produce byproducts such as isobutanol and other byproducts.

The temperature, pressure, and the catalyst volume provided in the hydrogenation reaction step are chosen in order to achieve a suitable per pass conversion of HPD, which gives a high selectivity to NPG and minimizes the formation of byproducts. Accordingly, the second reaction step may be operated at a temperature of from 110° C. to 170° C., preferably from 130° C. to 150° C., and a pressure of from 20 bar to 60 bar, preferably from 20 bar to 50 bar. The HPD content in the liquid feed to the second reaction step may be anywhere between 30-60 percent by weight, the balance being water, solvent, and byproducts. The molar ratio of hydrogen to HPD in the feed to the second reaction step may be anywhere between 10:1 and 3:1, preferably between 8:1 and 5:1.

The outlet stream from the hydrogenation reaction step contains unreacted hydrogen, NPG, and byproducts from both the aldol condensation and hydrogenation reaction steps. Highly pure NPG is separated from this stream by a suitable means such as crystallization or distillation. The solvent is also separated by a suitable means such as evaporation or distillation and recycled to the aldol condensation reactor. Particularly, recovering highly pure NPG by crystallization is preferable, since by doing so NPG can be separated from heavy byproducts such as esters without having to evaporate NPG. Crystallization of NPG can be performed using a slurry crystallizer with water as the crystallization solvent, or in a melt crystallizer without the presence of any crystallization solvent. If NPG is used as the solvent, the mother liquor from the crystallization step can be partially recycled to the aldol condensation reactor.

Figure 2:
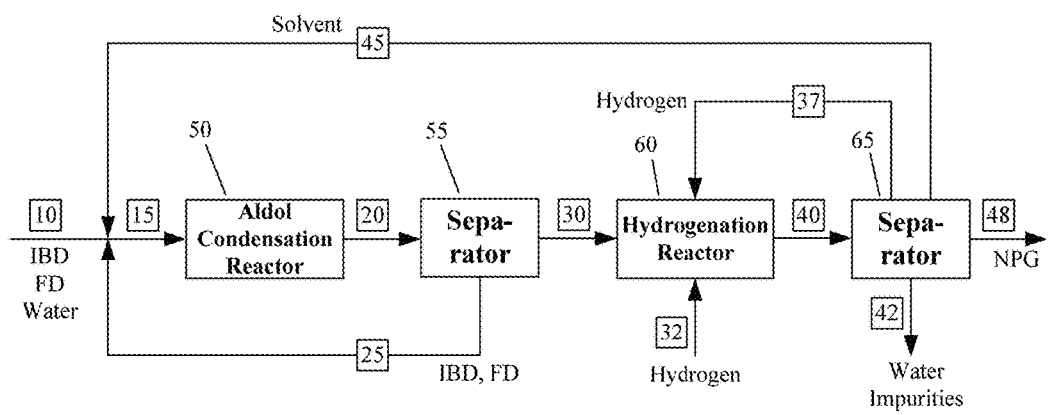
FIG. 2 shows a simplified flow diagram of a process for producing neopentyl glycol from isobutyraldehyde and formaldehyde according to the invention.

The method of the present invention is illustrated in FIG. 2. In general, the system is comprised of an aldol condensation reactor unit 50; a separator unit 55, a hydrogenation reactor unit 60, and a separator unit 65. Fresh feed 10 containing IBD, FD, and water is mixed with recycled IBD, FD, and solvent, and conveyed to reactor 50 where it is contacted with a suitable catalyst such that a part of the IBD and FD is converted to HPD via reaction (1). The outlet stream 20 contains unreacted IBD, unreacted FD, HPD, water, and impurities generated from side reactions in reactor 50. This stream is sent to a separator 55, which removes unreacted IBD and FD. The remaining mixture 30 is sent to reactor 60, where it is contacted with fresh hydrogen feed 32 and recycled hydrogen 37.

The hydrogenation reactor outlet 40 is preferably rich in NPG, and is sent to a separator 65, in which unreacted hydrogen, water and light impurities are recovered using a suitable method such as distillation. Unreacted hydrogen is returned to the second reactor 60 through line 37. Water and light impurities are purged from the process through line 42. High purity NPG is recovered through line 48 using a suitable method such crystallization or distillation. The solvent, which may contain some impurities, is recycled to the first reactor 50 through line 45.

Compared to the process known in the prior art, the method of the current invention does not require the use of a liquid catalyst such as trimethylamine for the aldol condensation step. Therefore, the need for an expensive catalyst separation step after the reaction can be eliminated. Instead, a solid catalyst such as an ion exchange resin catalyst, which can be easily separated from the reaction product, is used. The feed to the aldol condensation step is made homogeneous by adding a solvent that is miscible with both IBD and water. Furthermore, the use of a crystallization step to recover the product NPG avoids the need for evaporating NPG in order to separate it from heavy byproducts such as esters.

EXAMPLES

Experiments are provided below to further illustrate the system and method of the present invention. These experiments are provided for illustration purposes only and are not intended to limit the scope of the invention in any way.

Example 1

Aldol Condensation of Formaldehyde and Isobutyraldehyde

Mixtures of FD, IBD, and NPG with various FD:IBD molar ratios are prepared in proportions as indicated in TABLE 1. NPG is added as a solvent to ensure the reactant mixture is a homogenous liquid at room temperature. All experiments are conducted in a stainless steel tubular reactor 300 mm in length and 10 mm in diameter, equipped with adjustable heating control, filled with about 30 mL of Amberlyst A21 IER catalyst. The reactant mixture is continuously pumped through the catalyst bed in an upflow manner with a liquid hourly space velocity of 0.5 $h^{-1}$. The reactor temperature is kept at 80° C. and atmospheric pressure.

The results summarized in TABLE 1 are taken at steady-state condition, which is achieved after collecting approximately 12 bed volumes of reaction product. The results demonstrate that a reasonably high conversion of FD can be achieved, and the conversion of FD increases with increasing molar ratio of FD:IBD. The selectivity to HPD is relatively constant regardless of the FD:IBD ratio.

TABLE 1

| FD:IBD molar ratio | Feed Composition (percent by weight) | | | HPD in product (percent by weight) | Conversion (percent, based on FD) | Selectivity to HPD (percent, based on FD) |
|---|---|---|---|---|---|---|
| | FD | IBD | NPG | | | |
| 1.7:1 | 17.6 | 25.2 | 24.5 | 33.1 | 88.8 | 94.9 |
| 1.5:1 | 16.1 | 26.2 | 24.6 | 31.5 | 84.8 | 93.9 |

TABLE 1-continued

| FD:IBD molar ratio | Feed Composition (percent by weight) | | | HPD in product (percent by weight) | Conversion (percent, based on FD) | Selectivity to HPD (percent, based on FD) |
|---|---|---|---|---|---|---|
| | FD | IBD | NPG | | | |
| 1.3:1 | 15.0 | 28.5 | 26.1 | 32.4 | 79.5 | 94.8 |
| 1.05:1 | 13.2 | 31.1 | 29.7 | 29.8 | 68.0 | 95.4 |

FD = Formaldehyde,
IBD = Isobutyraldehyde,
NPG = Neopentyl Glycol,
HPD = Hydroxypivaldehyde

Example 2

Hydrogenation of Hydroxypivaldehyde

The reaction product from Example 1 is distilled to remove the unreacted aldehydes, then NPG is added to make up a hydrogenation reaction feed with a suitable composition as intended by one embodiment of this invention. A hydrogenation reaction experiment is conducted in a stainless steel tubular reactor 300 mm in length and 10 mm in diameter, filled with about 30 mL copper-based fixed bed catalyst (containing Cu, Co, Mn). The hydrogenation catalysts are reduced to metallic form by contacting with hydrogen at 200° C. prior to the reaction test.

A liquid feed consisting of 5.7 percent HPD, 70.6 percent NPG, 22.7 percent water, and 1 percent other impurities (by weight) is continuously pumped through the catalyst bed in an upflow manner with a liquid hourly space velocity of 8 $h^{-1}$. Hydrogen gas is mixed with the liquid feed at a hydrogen to HPD molar ratio of 7.5:1 before entering the fixed bed reactor. The reaction is conducted at a temperature of 150° C. and a pressure of 50 bar. At steady-state condition, which is achieved after collecting approximately 12 bed volumes of reaction product, the conversion of HPD is found to be 98.1 percent, with 99.3 percent selectivity to NPG.

Example 3

Simulated Experiment of NPG Production Process

Simulation results are provided below to illustrate the system and method of the present invention. These results are provided for illustration purposes only and are not intended to limit the scope of the invention in any way. Reference is made to the process block diagram shown in FIG. 2.

Pure IBD and formalin solution containing 37 percent FD, 59 percent water, and 4 percent methanol (by weight) are mixed with NPG as solvent, so that the final content of NPG in the feed to the aldol condensation reaction is about 26 percent by weight. The conversion of FD in the first reactor is 87 percent, with 93 percent selectivity towards HPD. In the second reactor, 99.9 percent of HPD is converted to NPG. The separation in block 65 is performed by a series of distillation followed by crystallization of NPG. TABLE 2 summarizes the total flow rate and compositions in percent by weight for major streams in the process, on the basis of 1000 kg/h NPG production.

TABLE 2

|  | Stream 10 | Stream 15 | Stream 20 | Stream 30 | Stream 32 | Stream 40 | Stream 48 |
|---|---|---|---|---|---|---|---|
| Total flow, kg/h | 1659 | 3375 | 3375 | 2542 | 26 | 2559 | 1000 |
| Composition, % by weight |  |  |  |  |  |  |  |
| IBD | 45.0 | 25.3 | 3.3 | 0 | 0 | 0 | 0 |
| FD | 20.3 | 15.8 | 6.6 | 0.096 | 0 | 0 | 0 |
| Hydrogen | 0 | 0 | 0 | 0 | 98.0 | 0 | 0 |
| Nitrogen | 0 | 0 | 0 | 0 | 2.0 | 0 | 0 |
| Water | 34.1 | 30.7 | 30.7 | 22.3 | 0 | 0.22 | 0 |
| HPD | 0 | 0.015 | 30.4 | 38.4 | 0 | 0.006 | 0.008 |
| Methanol | 0.54 | 0.27 | 0.27 | 0.35 | 0 | 2.0 | 0 |
| Isobutanol | 0 | 0.02 | 0.02 | 0 | 0 | 1.1 | 0.002 |
| NPG | 0 | 26.4 | 26.4 | 35.0 | 0 | 74.2 | 99.78 |
| Others | 0 | 0.1 | 2.4 | 3.0 | 0 | 0.6 | 0.21 |

As illustrated above, embodiments of the present invention provide significantly improved systems and methods for the production of neopentyl glycol. The present invention is not to be limited in scope by the specific embodiments disclosed in the examples which are functionally equivalent within the scope of this invention. Indeed, various modifications of the invention in addition to those shown and described herein will become apparent to those skilled in the art and are intended to fall within the appended claims.

As illustrated above, embodiments of the present invention provide significantly improved systems and methods for the production of neopentyl glycol. The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

We claim:

1. A method for producing neopentyl glycol from isobutyraldehyde, formaldehyde, and hydrogen, comprising the steps of:
    controlling the composition of feed to a first reaction step such that a homogeneous solution is formed, where the composition of the feed to the first reaction step is controlled such that a homogeneous solution is formed by adding a solvent that is miscible with both isobutyraldehyde and water, and where the solvent is comprised of neopentyl glycol at a concentration of 10% to 30% by weight in the feed to the first reaction step;
    introducing the homogeneous solution to an aldol condensation reactor in the first reaction step, where at least a portion of the isobutyraldehyde and formaldehyde undergo an aldol condensation reaction to form a reaction mixture comprising hydroxypivaldehyde, in the presence of a suitable solid catalyst;
    separating excess and unreacted aldehydes from the reaction mixture and recycling the aldehydes to the aldol condensation reactor;
    contacting hydroxypivaldehyde with hydrogen in a hydrogenation reactor in a second reaction step, where hydroxypivaldehyde is converted to neopentyl glycol in the presence of a suitable hydrogenation catalyst;
    isolating highly pure neopentyl glycol from the reaction mixture from the hydrogenation reactor; and
    recovering neopentyl glycol from the reaction mixture from the hydrogenation reactor, so that the neopentyl glycol can be recycled to the first reaction step.

2. The method according to claim 1, where the aldol condensation reaction occurs at a temperature of from 40° C. to 100° C., a pressure of from 1 bar to 5 bar, and a molar ratio of isobutyraldehyde to formaldehyde of 0.8:1 to 4:1.

3. The method according to claim 1, where the aldol condensation reaction occurs at a temperature of from 60° C. to 90° C., a pressure of from 1 bar to 2 bar, and a molar ratio of isobutyraldehyde to formaldehyde of 1:1 to 2:1.

4. The method according to claim 1, where the hydrogenation reaction occurs at a temperature of from 110° C. to 170° C., a pressure of from 20 bar to 60 bar, and a molar ratio of hydrogen to hydroxypivaldehyde in the feed to the second reaction step is between 10:1 and 3:1.

5. The method according to claim 1, where the hydrogenation reaction occurs at a temperature of from 130° C. to 150° C., a pressure of from 30 bar to 50 bar, and a molar ratio of hydrogen to hydroxypivaldehyde in the feed to the second reaction step is between 8:1 and 5:1.

6. The method according to claim 1, where the composition of the feed to the first reaction step is further controlled by adjusting the ratio of isobutyraldehyde, formaldehyde, and water.

7. The method according to claim 1, where the neopentyl glycol content in the feed to the first reaction step is between 15% and 25% by weight.

8. The method according to claim 1, where high purity neopentyl glycol is obtained by distillation.

9. The method according to claim 1, where high purity neopentyl glycol is obtained by crystallization.

10. The method according to claim 9, where the crystallization is a slurry crystallization process in the presence of water as solvent.

11. The method according to claim 9, where the crystallization is a melt crystallization process.

* * * * *